United States Patent
Pell et al.

(10) Patent No.: US 10,335,606 B2
(45) Date of Patent: *Jul. 2, 2019

(54) USE OF TRANSCRANIAL MAGNETIC STIMULATION TO MODULATE PERMEABILITY OF THE BLOOD-BRAIN BARRIER

(71) Applicant: BRAINSWAY, LTD., Jerusalem (IL)

(72) Inventors: Gaby Pell, Jerusalem (IL); Abraham Zangen, Jerusalem (IL); Yiftach Roth, Rechelim (IL); Alon Friedman, Mosherville (CA); Udi Vazana, Ashdod (IL)

(73) Assignee: BRAINSWAY, LTD., Jerusalem (IL)

( * ) Notice: Subject to any disclaimer, the term of this patent is extended or adjusted under 35 U.S.C. 154(b) by 5 days.

This patent is subject to a terminal disclaimer.

(21) Appl. No.: 15/498,696

(22) Filed: Apr. 27, 2017

(65) Prior Publication Data
US 2017/0291036 A1    Oct. 12, 2017

Related U.S. Application Data

(63) Continuation-in-part of application No. 14/378,427, filed as application No. PCT/IB2013/051171 on Feb. 13, 2013, now Pat. No. 9,636,517.

(60) Provisional application No. 61/597,850, filed on Feb. 13, 2012.

(51) Int. Cl.
*A61N 2/00* (2006.01)
*A61N 2/02* (2006.01)

(52) U.S. Cl.
CPC ............... *A61N 2/006* (2013.01); *A61N 2/02* (2013.01)

(58) Field of Classification Search
CPC .................................. A61N 2/004; A61N 2/02
See application file for complete search history.

(56) References Cited

U.S. PATENT DOCUMENTS

| | | | |
|---|---|---|---|
| 2006/0199992 A1* | 9/2006 | Eisenberg | A61N 1/40 600/14 |
| 2010/0087698 A1* | 4/2010 | Hoffman | A61N 2/006 600/13 |
| 2010/0172842 A1* | 7/2010 | Israeli | A61B 5/055 424/9.3 |
| 2012/0016174 A1* | 1/2012 | De Taboada | A61N 5/04 600/2 |

* cited by examiner

*Primary Examiner* — Christine H Matthews
*Assistant Examiner* — Joshua Daryl D Lannu
(74) *Attorney, Agent, or Firm* — Alphapatent Associates, Ltd; Daniel J. Swirsky; Ricki L. Simon (57) ABSTRACT

Transcranial magnetic stimulation (TMS) is used to modulate permeability of the blood brain barrier in a transient, safe and non-invasive manner. A conventional or deep TMS coil may be placed on a head in a vicinity of a tumor, for example. A series of magnetic pulses is provided to the brain with a tailored stimulation protocol. In one of many possible clinical applications, a pharmaceutical substance may be introduced during a time frame before, during or after providing the magnetic pulses to treat a tumor in the brain.

28 Claims, 6 Drawing Sheets

USE OF TRANSCRANIAL MAGNETIC STIMULATION TO MODULATE PERMEABILITY OF THE BLOOD-BRAIN BARRIER

CROSS-REFERENCES TO RELATED APPLICATIONS

The present application is a continuation-in-part application of U.S. application Ser. No. 14/378,427, filed Aug. 13, 2014, and issued on May 2, 2017, as U.S. Pat. No. 9,636,517, which is a U.S. National Phase Application under 35 U.S.C. 371 of International Application No. PCT/162013/051171, filed Feb. 13, 2013, which claims priority from U.S. Provisional Application Ser. No. 61/597,850, filed Feb. 13, 2012, each of which is incorporated herein by reference in its entirety.

FIELD AND BACKGROUND OF THE INVENTION

The present invention is directed to a method of modulating permeability of the blood brain barrier using transcranial magnetic stimulation (TMS).

The blood-brain barrier (BBB) is a separation of circulating blood from the brain extracellular fluid in the central nervous system (CNS). It occurs along all capillaries and consists of tight junctions around the capillaries that do not exist in normal circulation. The BBB prevents the entry of substances that are hydrophilic or possess a high molecular weight. Its purpose is mainly to protect the brain from the entry of toxins and bacteria. However, it also acts as an impermeable barrier to the entry of more than 95% of the most clinically useful neurotherapeutic agents.

A number of experimental approaches have been proposed to open the BBB. These include high-intensity focused ultrasound, magnetic nanoparticles, peptide carriers, photodynamic therapy and electrochemotherapy. However, many of these techniques are highly speculative and are still in the experimental stages of development. Similarly, a number of techniques exist for the local administration of drugs to brain tumors. These include inter-cerebral implantation (for example, gliadel wafers), intra-arterial drug administration and hyper-osmotic disruption. However, the efficiency of these techniques is doubtful, and the implementation is often non-localized and invasive.

There are a number of important circumstances in which a means of safe and controlled blood brain barrier disruption (BBBD) would be of great clinical significance. These include the treatment of tumors of the central nervous system (CNS) in which a transient opening of the BBB could permit the delivery of chemotherapeutic agents to the brain during the window of BBB disruption with a potentially huge impact on the treatment of cancerous tumors of the CNS. Similarly, a number of diseases such as epilepsy and auto-immune diseases such as multiple sclerosis are characterized by unwanted breaches in BBB patency which would benefit from a means to reduce the permeability of the BBB. A goal of controlled BBB disruption therefore includes both a means to increase and decrease the permeability of the BBB.

Thus, it would be highly advantageous to have a method for blood brain barrier permeability control, which is safe, non-invasive, focused and reversible.

SUMMARY OF THE INVENTION

There is provided, in accordance with embodiments of the present invention, a transcranial magnetic stimulation (TMS) coil used for modulating permeability of the blood brain barrier (BBB). The coil may be a conventional TMS coil or a deep TMS coil. A method for modulating permeability of the blood brain barrier includes providing a system for TMS, placing the system on the scalp, and providing a series of magnetic pulses to the brain via the system. The magnetic pulses are applied with a range of stimulation parameters designed for optimal modulation of the BBB.

In further features in embodiments of the present invention, the providing of magnetic pulses may be done in ranges of frequency, amplitudes and numbers of pulses and combinations thereof. In some embodiments of the invention, the stimulation frequency may be in a range of 0.2-2 Hz. At this stimulation frequency, the combination of stimulation amplitude taken with the number of stimulation pulses may vary. For example, the stimulation amplitude may be at least 120% together with at least 100 stimulation pulses. The stimulation amplitude may be in a range of at least 110-120% together with at least 300 stimulation pulses. The stimulation amplitude may be in a range of approximately between 100-110%, with at least 400 stimulation pulses. The stimulation amplitude may be between 80-100%, with at least 800 stimulation pulses. In other embodiments, the stimulation frequency may be greater than 2 Hz. At this stimulation frequency, the stimulation amplitude taken with the number of stimulation pulses may vary. For example, the stimulation amplitude may be at least 130%, with at least 200 stimulation pulses. The stimulation amplitude may be between 120-130%, with at least 400 stimulation pulses. The stimulation amplitude may be between 110-120%, with at least 600 stimulation pulses. The stimulation amplitude may be between 100-110%, with at least 800 stimulation pulses. The stimulation amplitude may be between 80-100%, with at least 1600 stimulation pulses.

The series of magnetic pulses may be configured to result in a temporary increase in a permeability of the blood brain barrier for a period of time, such as approximately 45-60 minutes. The temporary increase in permeability may be for a period of at least 1 minute, and in some embodiments for at least 3 minutes, and yet additional embodiments for at least 5 minutes. The increase in permeability may be for a length of time that would enable administration of treatment to the brain, for example. The series of magnetic pulses may be configured to result in a temporary decrease in a permeability of the blood brain barrier for a period of time, such as approximately 45-60 minutes. The temporary decrease may be for a period of at least 1 minute, and in some embodiments for at least 3 minutes, and yet additional embodiments for at least 5 minutes.

In one embodiment, a subject with an intracranial tumor may be treated. Placement of the coil may be done at the periphery of the intracranial tumor or on a side of the scalp which is contralateral to the tumor. In embodiments of the present invention, the method may include administering a pharmaceutical substance to the subject. This administering may be done within a time frame of providing the magnetic pulses. In other embodiments, the BBB may be modulated for other purposes—for example, to reduce unwanted inflammation or immunomodulatory effects in conditions such as multiple sclerosis, or to treat the growing number of conditions whose etiology is being linked to pathological changes in BBB permeability such as schizophrenia, epilepsy and Alzheimer's Disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

BRIEF DESCRIPTIONS OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that embodiments of the present invention may be practiced without these specific details. In other instances, well-known methods, procedures, components and structures may not have been described in detail so as not to obscure the present invention.

The present invention relates to a system and method for modulating permeability of the BBB using a TMS coil. Further advantages of the design of the catheter of the present invention will be described hereinbelow.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

The present invention is directed to a method for modulating permeability of the blood brain barrier using transcranial magnetic stimulation (TMS). TMS is a proven and safe technique for the non-invasive stimulation of neurons and has been shown to be beneficial in the treatment of a variety of neurological disorders such as depression. The vascular tone of the brain capillaries is largely under neurogenic and muscular control. The stimulation of the vascular neurons and smooth muscle by TMS may therefore be able to influence the permeability of the BBB via either a direct or indirect mechanism.

Early studies of TMS using standard stimulation parameters and coils showed no disruptive effect on the BBB. In the present invention, it has been found that the application of TMS with a specific set of stimulation parameters may indeed have an effect on the temporary disruption of the BBB under certain conditions.

Figure 1:
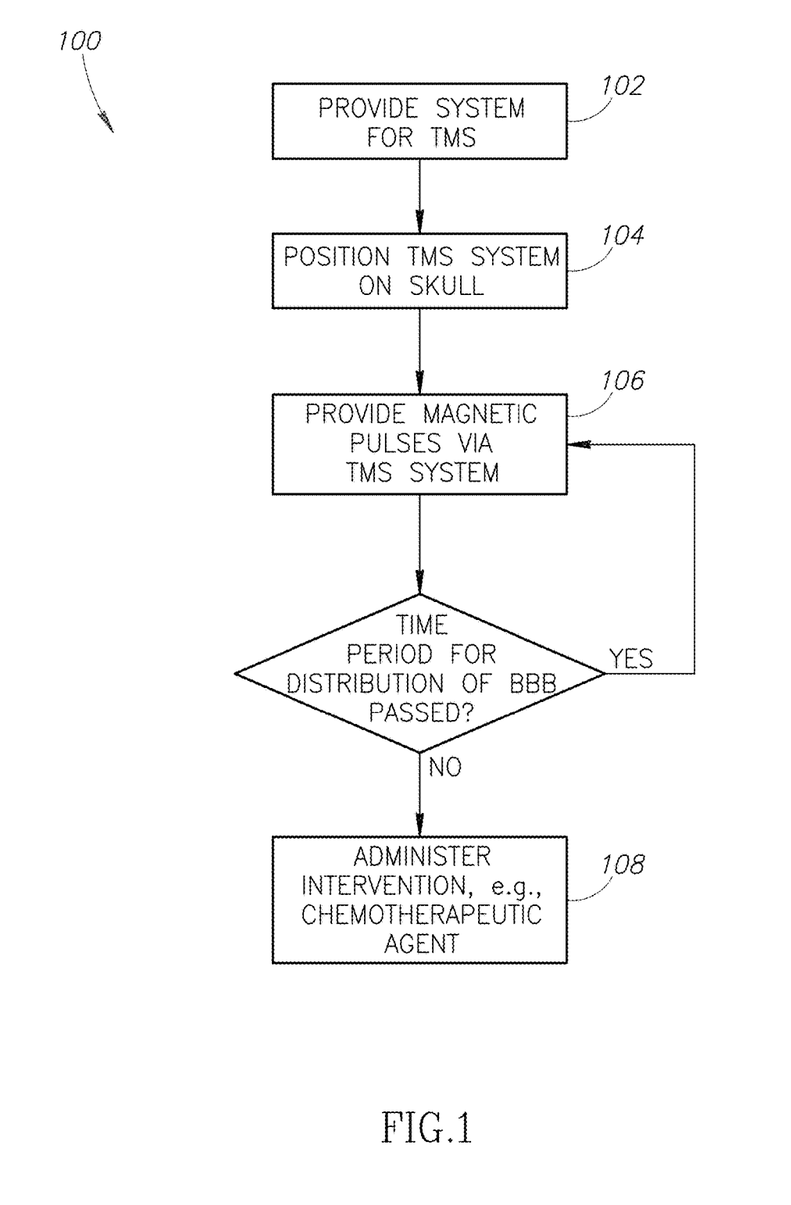
FIG. 1 is an illustrative flowchart of a method of BBB disruption for treatment of CNS tumors, in accordance with embodiments of the present invention.

Reference is now made to FIG. 1, which is a flow-chart diagram of a method 100 of modulating permeability of the blood brain barrier, in accordance with embodiments of the present invention. First, a system for transcranial magnetic stimulation (TMS) is provided (step 102). In some embodiments, the TMS system is a system for deep TMS, such as the H1 coil (Brainsway, Inc.). In other embodiments, a standard FIG. 8 coil or any other coil suitable for TMS is provided. The TMS system is positioned (step 104) on the skull, on or adjacent to the area of the brain to be treated, and magnetic pulses are provided (step 106) via the TMS system. Placement of the coil may be done at the periphery of an intracranial tumor or on a side of the scalp which is contralateral to a tumor. In some embodiments, a series of pulses is provided using a prescribed TMS coil configuration in conjunction with a prescribed range of frequencies and stimulation amplitudes. In some embodiments, low frequency repetitive deep TMS (0.5-2 Hz) applied in very supra-threshold amplitudes (>120% of resting motor threshold (rMT) may be used. This administration of magnetic pulses in this configuration has been found in the present invention to lead to a transient increase of the permeability of the BBB. It should be readily apparent that other frequencies and amplitudes are possible and are included within the scope of the invention.

In some embodiments, the magnetic pulses are provided in a range of at least 0.2 Hz stimulation frequency, at least 80% of resting motor threshold stimulation amplitude, and at least 100 stimulation pulses.

Different ranges of frequency, amplitudes and numbers of pulses and combinations thereof may be used. In embodiments of the invention, the stimulation frequency may be in a range of 0.2-2 Hz. At this stimulation frequency, the stimulation amplitude may be at least 120% together with at least 100 stimulation pulses. The stimulation amplitude may be in a range of at least 110-120% together with at least 300 stimulation pulses. The stimulation amplitude may be in a range of approximately between 100-110%, with at least 400 stimulation pulses. The stimulation amplitude may be between 80-100%, with at least 800 stimulation pulses.

In other embodiments, the stimulation frequency may be greater than 2 Hz. At this stimulation frequency, the stimulation amplitude may be at least 80%, with at least 200 stimulation pulses. The stimulation amplitude may be between 120-130%, with at least 400 stimulation pulses. The stimulation amplitude may be between 110-120%, with at least 600 stimulation pulses. The stimulation amplitude may be between 100-110%, with at least 800 stimulation pulses. The stimulation amplitude may be between 80-100%, with at least 1600 stimulation pulses.

The series of magnetic pulses may be configured to result in a temporary increase in a permeability of the blood brain barrier for a period of time, such as at least one minute, at least 3 minutes, at least 5 minutes, 10-90 minutes, 30-90 minutes, approximately 45-60 minutes or any other suitable time range. The series of magnetic pulses may also be configured to result in a temporary decrease in a permeability of the blood brain barrier for a period of time, such as at least one minute, at least 3 minutes, at least 5 minutes, 10-90 minutes, 30-90 minutes, approximately 45-60 minutes or any other suitable time range.

In other embodiments, other periods of time may be used. For example, in some embodiments a range of 30-90 minutes may be used. In some embodiments a range of less than 30 minutes or greater than 90 minutes may be used. During this time window, the increased permeability of the BBB can be exploited, for example to administer (step 108) an intervention, such as introducing a chemotherapeutic agent in order to treat a tumor of the CNS.

Other uses for modulating the BBB, in accordance with the present invention, include increasing BBB permeability for administering medications for brain disorders, and decreasing BBB permeability in patients with neurological or psychiatric disorders where the BBB has abnormally increased permeability.

Experimental Data

A study was conducted to investigate the use of a deep TMS system to disrupt the BBB in a temporary and controlled manner.

The described study used a combined approach of pre-clinical experiments in animals to demonstrate effectiveness and define TMS parameters, followed by a pilot study in patients with brain tumors using magnetic resonance imaging (MRI) to investigate the BBB patency in a non-invasive and potentially quantitative manner.

Pre-clinical experiments: Pre-clinical experiments were carried out at Soroka Hospital in Beer Sheva, Israel, using rats (REAL (i.e. active) coil, n=10; SHAM (i.e. placebo) coil, n=5). The cortex was exposed, and TMS stimulation was carried out using a small circular coil. Results were measured by optical imaging using Evans Blue and Sodium Fluorescein (fluorescent dye), both dyes with high-molecular weight that normally remain within the vasculature. Quantification was carried out with $K_{trans}$.

Figure 2A:
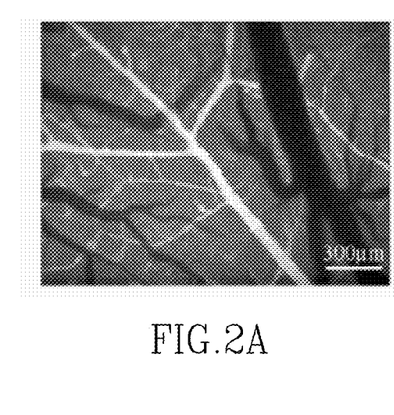
FIGS. 2A-2F are illustrations of the results of animal experiments showing BBB disruption using transcranial magnetic stimulation.
Figure 2B:
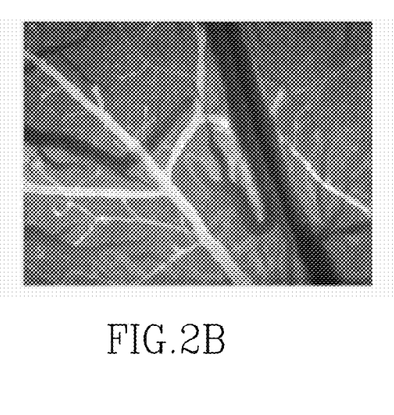
Figure 2C:
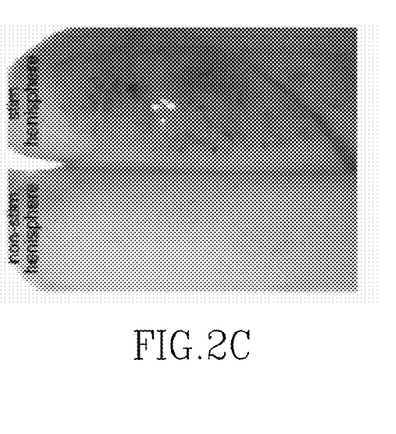
Figure 2D:
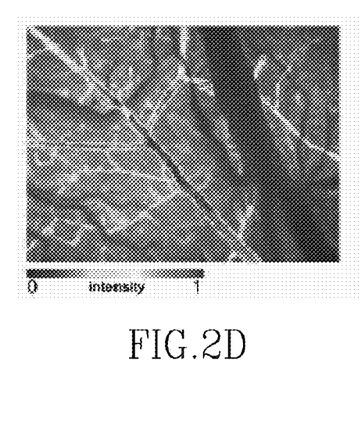
Figure 2E:
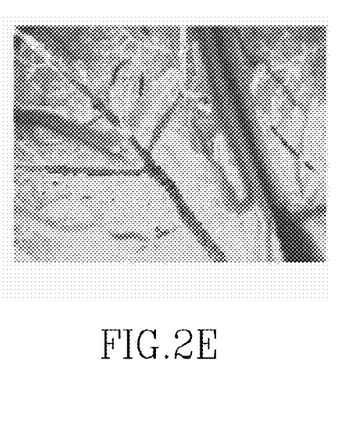
Figure 2F:
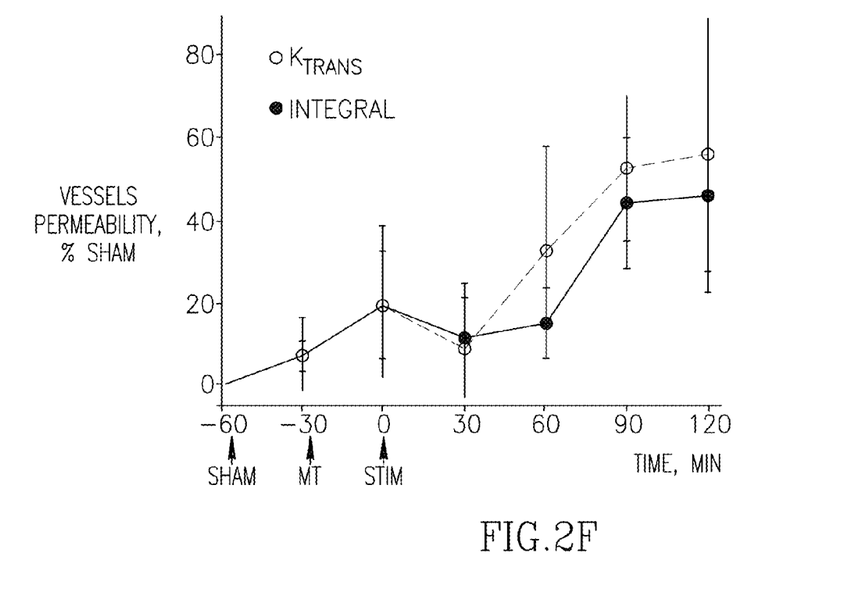

These dyes were clearly observed in the parenchyma (tissue space) after exposure to a stimulation protocol using high-intensity, low frequency rTMS (stimulation protocol: 1 Hz, 130% of resting motor threshold, 250 pulses). The BBB appeared to open immediately, and then to close after approximately 60 minutes. No such BBB disruption was observed following SHAM stimulation. Other stimulation protocols were found to modulate the BBB permeability to greater or lesser extents. Reference is now made to FIGS. 2A-2F, which are illustrations of the results of animal experiments showing BBB disruption using transcranial magnetic stimulation. Fluorescent images of surface vessels are shown before (SHAM) and after (REAL) TMS, using a particular stimulation protocol (raw data in FIGS. 2A and 2B; permeability data using $K_{trans}$ in FIGS. 2D and 2E). Vasodilation of the blood vessels (FIGS. 2A vs 2B) and the presence of the injected tracer around the vessels as indicated by increased value of the permeability measure, $K_{trans}$, in the extravascular region (FIGS. 2D vs 2E) clearly indicate a process resulting in BBB opening. Reference is made to FIG. 2C, where staining of the stimulated hemisphere following Evans-blue injection confirms BBB disruption, as indicated by presence of the blue dye within the parenchyma. One hemisphere, which was subject to TMS, shows extravasation of the dye from the intravascular to extravascular compartment (indicated by a brightening of the area surrounding the blood vessels), whereas the other hemisphere, which was not subject to TMS, does not. FIG. 2F is a graphical illustration of the permeability (i.e, $K_{trans}$) measurement, showing the time frame of the opening of the BBB.

In conclusion, the animal experiments showed consistent opening of the BBB. Modulation of the BBB was dependent on the stimulation protocol, and in one example, a protocol utilizing a combination of low frequency and high amplitude was found to be successful. Permeability quantification with $K_{trans}$ results show the dynamics of the opening. BBB appears to open immediately, and close within approximately 45-60 minutes.

Clinical experiments: 19 patients with glioblastoma multiforme were admitted to the feasibility study (carried out in La Sapienza Hospital, Rome). Stimulation with the deep TMS system on an area of the cortex in the periphery of the tumor core was followed by the injection of a MRI-visible contrast agent (Gadolinium-DTPA) and a series of dynamic MRI scans. Stimulation with REAL and SHAM TMS coils were carried out on different days with their order counter-balanced. TMS stimulation was carried out using a deep TMS coil designed and assembled by Brainsway Inc, at a frequency of 1 Hz and with an amplitude of 130% of resting motor threshold in a series of stimulation trains comprising 250 pulses in total. The train duration was 50 sec, with inter-train intervals of 60 sec and the total number of trains was 5. A smaller subset of 4 control, healthy subjects were also examined in this way.

Figure 3:
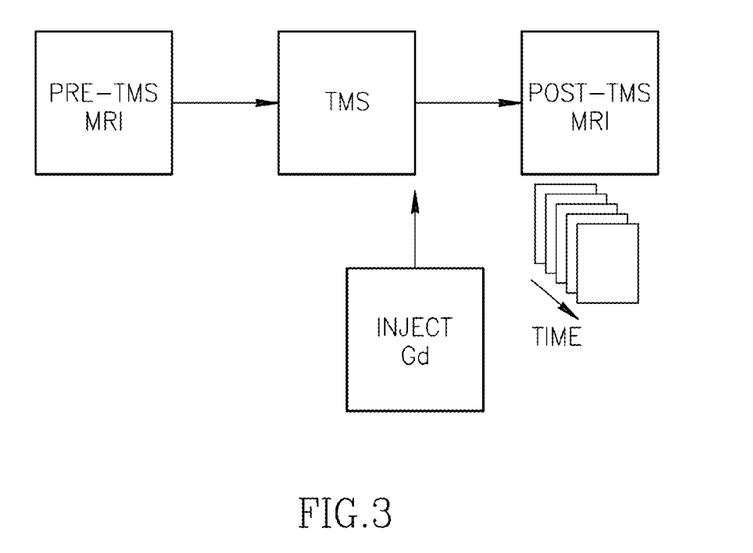
FIG. 3 is a schematic view of a procedure used in human experiments showing BBB disruption using transcranial magnetic stimulation.

Reference is now made to FIG. 3, which is a flow chart illustration showing the method of the clinical experiments. The subject was placed in the magnetic resonance imaging (MRI) scanner for the acquisition of pre-stimulation MRI images, including baseline anatomical scans. The subject was then removed from the MRI scanner in order to receive the TMS stimulation. Following the stimulation, the contrast agent was injected into a vein and the subject immediately returned to the scanner for the acquisition of a series of post-stimulation scans. Two sessions of stimulation were carried out, in each case preceded and followed by MR imaging (pre-TMS MRI and post-TMS MRI respectively).

Figure 4A:
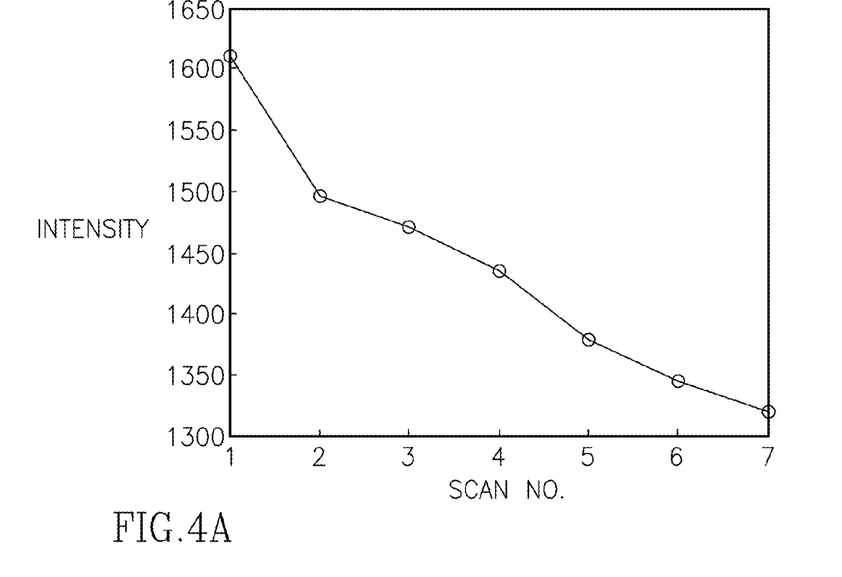
FIGS. 4A and 4B are graphical illustrations of signal decay profiles expected in different tissue types following injection of Gadolinium (Gd) using longitudinal contrast-enhanced MR imaging.
Figure 4B:
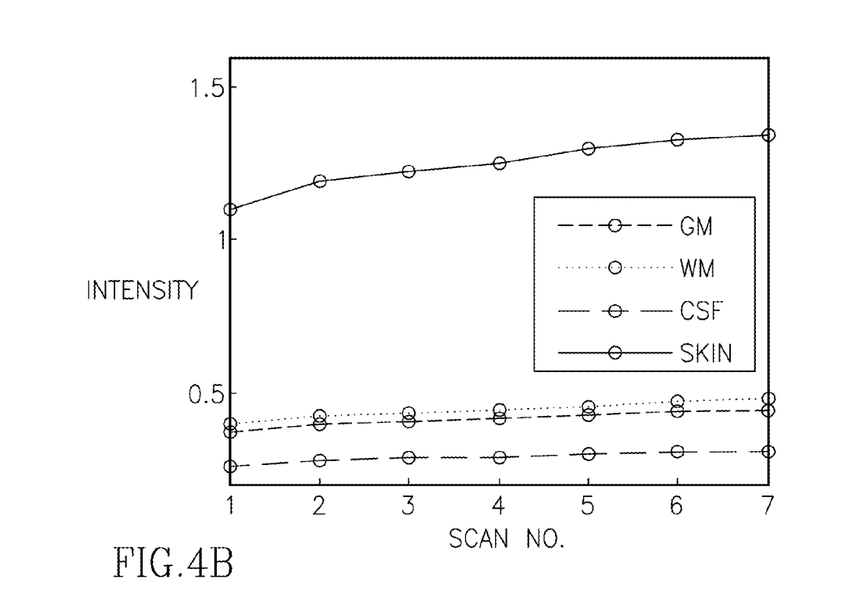

Analysis was carried out by a series of processing steps. Reference is now made to FIGS. 4A and 4B, which are graphical illustrations showing representative longitudinal time-series data. The slope of this signal change was calculated and reflects the kinetics of the contrast agent between the parenchymal and vascular compartments. The degree of BBB permeability is indicated by the amplitude and sign of the fitted slope parameter. Different signal decay profiles are expected in different tissue types following injection of Gadolinium (Gd) using longitudinal contrast-enhanced MR imaging. The vascular signal, shown in FIG. 4A, normally shows a rapid decline of intensity over time as the tracer washes out of the vascular bed, while tissue signal, shown in FIG. 4B, displays a gradual rise in intensity if the BBB permeability is increased.

Results

Figure 5:
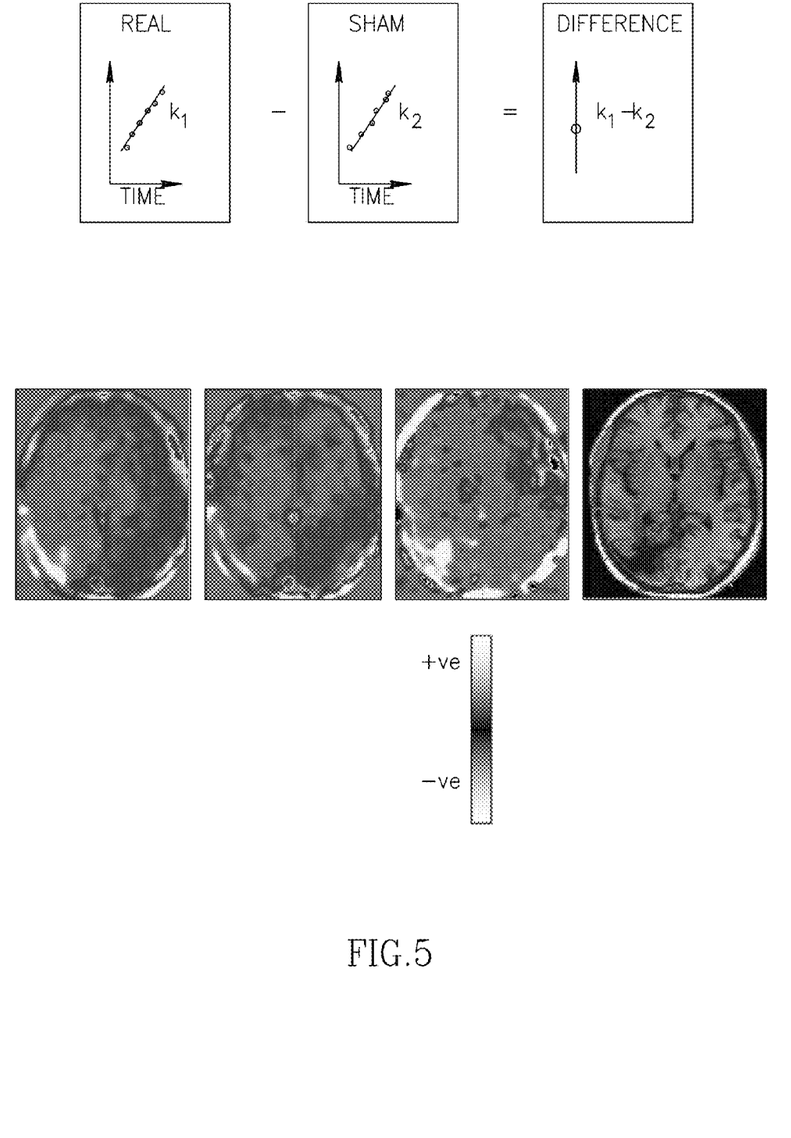
FIG. 5 is an illustration of images of the brain of a subject from human experiments.

Reference is now made to FIG. 5, which is a representative illustration from the brain of one of the patients in the pilot human study following REAL and SHAM stimulation. The standard anatomical scan is also shown on the right showing the resected tumor zone. Parametric images of the fitted slope calculated at each voxel are shown for REAL and SHAM stimulation. The slope is a direct measure of BBB modulation. A zone of increased slope is clearly observed in the REAL case that is highlighted by subtracting the images (REAL-SHAM). In more than 60% of the patients with a contrast-enhancing tumor, a similar pattern was observed in the imaging data with a clearly depicted a zone of increased contrast agent intravascular-to-parenchyma washout following the REAL stimulation in contrast to the SHAM stimulation. The accelerated contrast agent kinetics are a strong indication of BBB disruption following the TMS stimulation. Changes were mainly observed in the tumor zone where the BBB is known to be abnormally permeable following rapid neovascularization as a consequence of tumor growth. This property of the BBB in the tumor zone is known as the enhanced permeability and retention (EPR) effect. However, there was also observed a tendency of increased stimulation-induced BBB permeability in extra-tumoral tissue, whether ipsilateral or contralateral to the tumor zone, which indicates an opening of the BBB. This is significant since these areas are normally largely impermeable to chemotherapeutic agents due to their intact BBB but are the key sites for the spread of the tumor via microgliomal infiltration and proliferation. The technique therefore offers the potential of improved treatment outcome by accompanying drug delivery with the controlled reversible BBB disruption.

Figure 6:
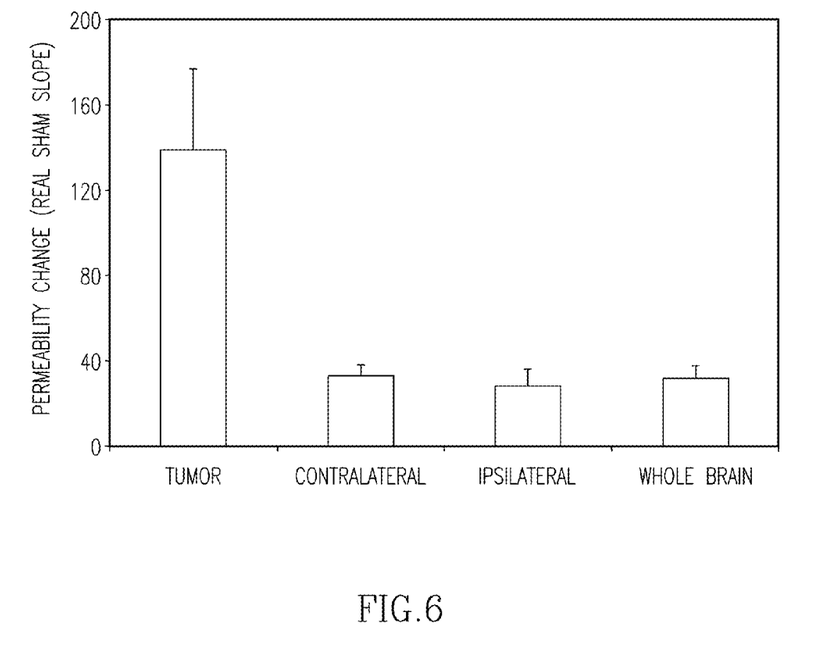
FIG. 6 is a graphical view of summary BBB permabililty measures over different areas of tissue obtained in REAL and SHAM stimulation states in human experiments.

Reference is now made to FIG. 6, which is a graphical illustration of summary BBB permeability measures over different areas of tissue obtained in REAL and SHAM stimulation states averaged over all the human patients in the study. Changes of stimulation-induced BBB permeability are shown over tissue regions that included the resected tumor zone itself, the hemisphere ipsilateral to the tumor (excluding the tumor zone), the contralateral hemisphere, and the whole brain (excluding the tumor zone). A significant finding of significantly enhanced permeabilily was consistently found following the REAL stimulation, in comparison to the SHAM stimulation session (p<0.05, 1-tailed, Wilcoxon signed-rank test).

Conclusions: The pre-clinical and clinical studies clearly demonstrated the ability of tailored TMS hardware and stimulation parameters to transiently disrupt the BBB. Both in an invasive animal model and in a pilot series of human subjects with CNS tumors, the ability to transiently increase BBB permeability was demonstrated.

Deep TMS represents the first known technique that has been shown to successfully increase the permeability of the BBB in a group of human subjects in a safe, non-invasive and controlled manner.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for modulating permeability of a blood brain barrier, the method comprising:
   providing a system for transcranial magnetic stimulation;
   placing said system on a scalp; and
   providing a series of magnetic pulses to a brain via the system, said providing done in a range of at least 0.2 Hz stimulation frequency, greater than 120% of resting motor threshold stimulation amplitude, and at least 100 stimulation pulses, wherein said series of magnetic pulses is configured to temporarily increase permeability of the blood brain barrier, wherein the temporary increase is for a period of at least 1 minute.

2. The method of claim 1, wherein said providing a series of magnetic pulses is done in a range of 0.2-2 Hz stimulation frequency.

3. The method of claim 1, wherein said providing a series of magnetic pulses is done with a stimulation amplitude of between 120-130% of the resting motor threshold stimulation amplitude and with at least 400 stimulation pulses.

4. The method of claim 1, wherein said providing a series of magnetic pulses is done with a stimulation amplitude of at least 130% of the resting motor threshold stimulation amplitude.

5. The method of claim 1, wherein said providing a system for transcranial magnetic stimulation and said placing said system on a scalp comprises providing and placing a figure—8 TMS coil on the scalp.

6. The method of claim 1, wherein said providing a system for transcranial magnetic stimulation and said placing said system on a scalp comprises providing and placing a deep TMS coil on the scalp.

7. The method of claim 1, wherein said temporary increase is for a period of at least 3 minutes.

8. The method of claim 1, wherein said temporary increase is for a period of at least 5 minutes.

9. The method of claim 1, wherein said placing is done at a periphery of an intracranial tumor.

10. The method of claim 1, wherein said placing is done on a side of the scalp which is contralateral to a tumor.

11. The method of claim 1, further comprising:
    within a predetermined time frame before, during or after said providing the magnetic pulses, administering a pharmaceutical substance to the brain.

12. A system for modulating permeability of the blood brain barrier, the system comprising:
    a transcranial magnetic stimulation coil for transcranial magnetic stimulation and configured to:
    be placed on a scalp; and provide a series of magnetic pulses in a range of at least 0.2 Hz stimulation frequency, with a stimulation amplitude of between 120-130% of resting motor threshold stimulation amplitude, and at least 400 stimulation pulses, wherein said series of magnetic pulses is configured to temporarily change permeability of the blood brain barrier (BBB) for a period of at least 1 minute.

13. The system of claim 12, wherein said coil is configured to provide said series of magnetic pulses in a range of 0.2-2 Hz stimulation frequency.

14. The system of claim 12, wherein said coil is a figure-8 TMS coil.

15. The system of claim 12, wherein said coil is an H-coil for deep TMS.

16. The system of claim 12, wherein said coil is configured to provide said series of magnetic pulses configured to temporarily change the permeability of the BBB for a period of at least 3 minutes.

17. The system of claim 12, wherein said coil is configured to provide said series of magnetic pulses configured to temporarily increase the permeability of the BBB.

18. The system of claim 12, wherein said coil is configured to provide said series of magnetic pulses configured to temporarily decrease the permeability of the BBB.

19. A system for modulating permeability of the blood brain barrier (BBB), the system comprising:
a transcranial magnetic stimulation coil for transcranial magnetic stimulation, said transcranial magnetic stimulation coil is an H-coil for deep TMS, said transcranial magnetic stimulation coil configured to:
be placed on a scalp; and
provide a series of magnetic pulses of at least 0.2 Hz stimulation frequency, with a stimulation amplitude of between 120-130% of resting motor threshold stimulation amplitude and with at least 400 stimulation pulses, wherein said series of magnetic pulses is configured to temporarily change permeability of the blood brain barrier for a period of at least 1 minute.

20. The system of claim 19, wherein said coil is configured to provide said series of magnetic pulses configured to temporarily change the permeability of the BBB for a period of at least 3 minutes.

21. The system of claim 19, wherein said coil is configured to provide said series of magnetic pulses configured to temporarily increase the permeability of the BBB.

22. A system for modulating permeability of the blood brain barrier, the system comprising:
a transcranial magnetic stimulation coil for transcranial magnetic
stimulation and configured to:
be placed on a scalp; and
provide a series of magnetic pulses in a range of at least 0.2 Hz stimulation frequency, greater than 120% of resting motor threshold stimulation amplitude, and at least 100 stimulation pulses, wherein said series of magnetic pulses is configured to temporarily decrease permeability of the blood brain barrier (BBB) for a period of at least 1 minute.

23. The system of claim 22, wherein said coil is configured to provide said series of magnetic pulses in a range of 0.2-2 Hz stimulation frequency.

24. The system of claim 22, wherein said coil is configured to provide said series of magnetic pulses with a stimulation amplitude of between 120-130% of the resting motor threshold stimulation amplitude and with at least 400 stimulation pulses.

25. The system of claim 22, wherein said coil is configured to provide said series of magnetic pulses with a stimulation amplitude of at least 130% of the resting motor threshold stimulation amplitude.

26. The system of claim 22, wherein said coil is a figure-8 TMS coil.

27. The system of claim 22, wherein said coil is an H-coil for deep TMS.

28. The system of claim 22, wherein said coil is configured to provide said series of magnetic pulses configured to temporarily change the permeability of the BBB for a period of at least 3 minutes.

* * * * *